United States Patent [19]

Clemence et al.

[11] Patent Number: 5,043,347
[45] Date of Patent: Aug. 27, 1991

[54] INDANES AND ANALGESIC COMPOSITIONS AND METHODS THEREOF

[75] Inventors: Francois Clemence; Odile Le Martret, both of Paris; Francoise Delevallee, Fontenay sous Bois; Michel Fortin, Paris, all of France

[73] Assignee: Roussel Uclaf, Paris, France

[21] Appl. No.: 438,526

[22] Filed: Nov. 17, 1989

Related U.S. Application Data

[62] Division of Ser. No. 86,996, Aug. 19, 1987.

[30] Foreign Application Priority Data

Aug. 21, 1986 [FR] France ................................ 86 11927
Jul. 3, 1987 [FR] France ................................ 87 09450

[51] Int. Cl.⁵ ..................... A61K 31/40; C07D 405/02
[52] U.S. Cl. ..................................... 514/409; 548/407
[58] Field of Search ........................ 548/407; 514/409

[56] References Cited

U.S. PATENT DOCUMENTS

| | | | |
|---|---|---|---|
| 4,359,476 | 11/1982 | Kaplan | 548/407 X |
| 4,360,531 | 11/1982 | McMillan | 548/407 X |
| 4,460,600 | 7/1984 | Kaplan | 546/234 X |
| 4,466,977 | 8/1984 | McMillan | 548/578 X |
| 4,876,269 | 10/1989 | Penney | 514/429 |

Primary Examiner—Joseph Paul Brust
Assistant Examiner—Jacqueline Haley
Attorney, Agent, or Firm—Bierman and Muserlian

[57] ABSTRACT

A compound selected from the group consisting of enantiomers and diastereoisomer forms and mixtures thereof of the formula

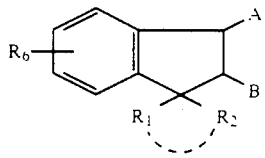

17 Claims, No Drawings

INDANES AND ANALGESIC COMPOSITIONS AND METHODS THEREOF

PRIOR APPLICATION

This application is a division of U.S. patent application Ser. No. 086,996 filed Aug. 19, 1987.

OBJECTS OF THE INVENTION

It is an object of the invention to provide the novel indanes of formula I and their non-toxic, pharmaceutically acceptable acid addition salts and a novel process and intermediates for their preparations.

It is another object of the invention to provide novel central analgesic compositions and a novel method of inducing central analgesic activity in warm-blooded animals.

These and other objects and advantages of the invention will become obvious from the following detailed description.

THE INVENTION

The novel compounds of the invention are selected from the group consisting of enantiomers and diastereoisomer forms and mixtures thereof of the formula

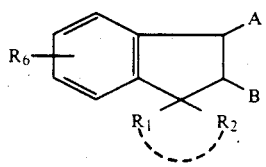

I wherein $R_6$ is selected from the group consisting of hydrogen, halogen and alkyl and alkoxy of 1 to 5 carbon atoms, $R_1$ and $R_2$ are individually hydrogen or alkyl of 1 to 5 carbon atoms or taken together with the carbon atoms to which they are attached form a cycloalkyl of 3 to 6 carbon atoms optionally containing a heteroatom selected from the group consisting of —S—, —O— and —N—, one of A and B has the formula

and the other has the formula

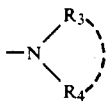

R is selected from the group consisting of hydrogen and alkyl of 1 to 5 carbon atoms, Z is selected from the group consisting of —$(CH_2)_n$—, branched alkylene of 2 to 8 carbon atoms and —$CH_2O$—, n is an integer of 0 to 5, X, X' and X" are individually selected from the group consisting of hydrogen, alkyl and alkoxy of 1 to 4 carbon atoms, halogen, —OH, —$CF_3$, —$NO_2$, —$NH_2$, mono and dialkylamino of 1 to 4 alkyl carbon atoms and sulfamino, $R_3$ and $R_4$ are individually selected from the group consisting of hydrogen and alkyl of 1 to 5 carbon atoms or taken together with the nitrogen atom to which they are attached form a 5 to 6 member heterocycle optionally containing a member of the group consisting of —O—, —S— and $$-\overset{R_1'}{\underset{|}{N}}-,$$

$R_1'$ is hydrogen or alkyl of 1 to 4 carbon atoms and their non-toxic, pharmaceutically acceptable acid addition salts.

When $R_1$, $R_2$, $R_3$, $R_4$, $R_6$, R, X, X' and X" are alkyl, they are preferably methyl, ethyl n-propyl or isopropyl but may also be n-butyl, isobutyl or n-pentyl. Examples of cycloalkyl formed by $R_1$ and $R_2$ and the carbon atoms to which they are attached are cyclopropyl, cyclobutyl, cyclopentyl and cyclohexyl. Examples of the cycloalkyl containing an oxygen, sulfur or nitrogen in the ring are tetrahydropyran, tetrahydrothiapyran and piperidinyl.

When Z is —$(CH_2)_n$—, n is preferably 0 or 1 and when Z is a branched alkylene, it is preferably alkylene substituted with methyl or ethyl such as 1,1-ethanediyl, methyl-1-ethanediyl-1,2, methyl-1 or -2-propanediyl-1,2 and ethyl-1-ethanediyl-1,2.

When $R_6$, X, X' and X" are alkoxy, they are preferably methoxy or ethoxy but they may be other alkoxys such as propoxy, isopropoxy and linear and branched butoxy and when they are halogen, they are preferably chlorine but may be fluorine, iodine or bromine. When X, X' and X" are monoalkylamino or dialkylamino, the alkyls are preferably methyl or ethyl.

Examples of heterocycles formed by $R_3$ and $R_4$ and the nitrogen to which they are attached are pyridinyl, piperazinyl, methylpiperazinyl, ethylpiperazinyl, propylpiperazinyl, piperidinyl, morpholinyl and pyrrolidinyl.

Examples of suitable acids to form the non-toxic, pharmaceutically acceptable acid addition salts are inorganic acids such as hydrochloric acid, hydrobromic acid, sulfuric acid, nitric acid and phosphoric acid and organic acids such as formic acid, acetic acid, propionic acid, maleic acid, fumaric acid, tartaric acid, succinic acid, citric acid, oxalic acid, glyoxylic acid and aspartic acid, alkanesulfonic acids, such as methanesulfonic acid, arylsulfonic acids such as benzene sulfonic acid and arylcarboxylic acids such as benzoic acid.

Among the preferred compounds of formula I are those wherein A and B have the trans configuration, those wherein

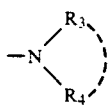

has $R_3$ and $R_4$ both as methyl or together with the nitrogen form pyrrolidine, piperidine, or piperazine optionally substituted with alkyl of 1 to 3 carbon atoms, those in which

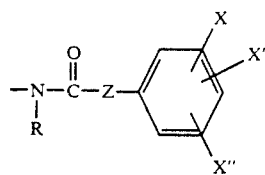

has R as hydrogen, methyl, or ethyl, Z is —CH$_2$O—.

or —(CH$_2$)$_n$— and n is 0 or 1, those wherein R$_1$ and R$_2$ are both hydrogen or methyl or together with the carbon atoms form tetrahydropyran and those wherein X, X' and X" are individually selected from the group consisting of hydrogen, methyl, ethyl, methoxy, ethoxy, —NO$_2$, sulfamino —CF$_3$ or chlorine and their non-toxic, pharmaceutically acceptable acid addition salts.

Examples of specific preferred compounds of formula I are

[trans(±)]3,4-dichloro-N-[2,3-dihydro-2-(1-pyrrolidinyl)-1H-inden-1-yl]-N-methyl-benzene-acetamide,

[trans(±)]N-[2,3-dihydro-2-(1-pyrrolidinyl)-1H-inden-1-yl]-N-methyl-3-nitro-benzene-acetamide,

[trans(±)]N-[2,3-dihydro-2-(1-pyrrolidinyl)-1H-inden-1-yl]-N-methyl-4-nitro-benzene-acetamide,

[trans(±)]N-[2,3-dihydro-2-(1-pyrrolidinyl)-1H-inden-1-yl]-N-methyl-(4-trifluoromethyl)-benzene-acetamide,

[trans(±)]2-(3,4-dichlorophenoxy)-N-[2,3-dihydro-2-(1-pyrrolidinyl)-1H-inden-1-yl]-N-methyl-acetamide,

[trans(±)]3,4-dichloro-N-[2,3-dihydro-2-(dimethylamino)-1H-inden-1-yl]-N-methyl-benzene-acetamide,

[trans(±)]N-[2,3-dihydro-2-(1-pyrrolidinyl)-1H-inden-1-yl]-N-methyl-4-nitro-benzene-acetamide (isomer A), and their non-toxic, pharmaceutically acceptable acid addition salts.

The novel process of the invention for the preparation of the compounds of formula I wherein A and B have the trans configuration comprises reacting a compound of the formula

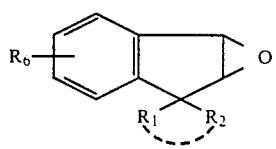

wherein R$_6$, R$_1$ and R$_2$ have the above definition with a compound of the formula

wherein R has the above definition and R$_5$ is an amine protective group, preferably benzyl to obtain a compound of the formula

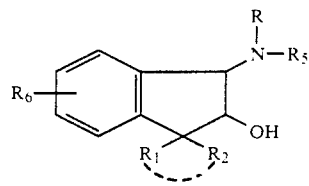

the hydroxy group is activated and reacted with an amine of the formula

wherein R$_3$ and R$_4$ have the above definitions to obtain a compound of the formula

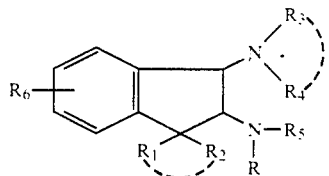

removing the R$_5$ group to obtain a compound of the formula

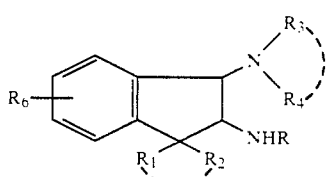

reacting the latter with an acid or a functional derivative thereof of the formula

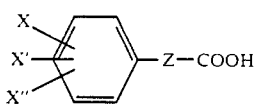

wherein Z, X, X' and X" have the above definitions to obtain a compound of formula I wherein A is

and R is

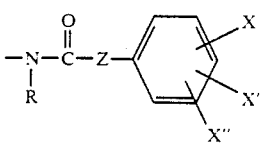

or the compound of formula II is reacted with an amine of the formula

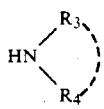

to form a compound of the formula

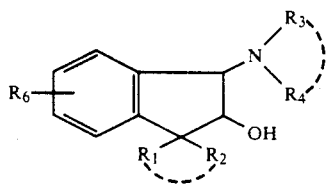

activating the hydroxyl of the latter and reacting with an amine of the formula

NH₂—R   X wherein R has the above definitions to obtain a compound of the formula

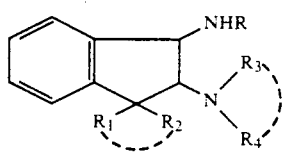

and reacting the latter with an acid of formula VIII or a functional derivative thereof to obtain a compound of formula I wherein A is

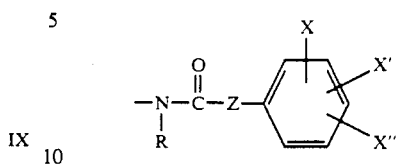

and B is

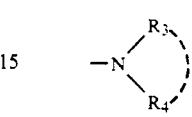

and optionallly resolving the latter and/or forming the acid addition salts thereof.

Preferably, the hydroxyl functions of formulae IV and IX are activated with methanesulfonyl chloride and the protective group R₅ of formula VI is benzyl which can be removed by catalytic hydrogenation in the presence of a palladium catalyst. The activation of the hydroxyl of the compounds of formula VIII is effected in the presence of carbonyldiimidazole and the acids of formula VIII are used in the acid chloride or mixed anhydride form. The resolution of the compounds of formula I can be effected by known methods.

The process of the invention to form the compounds of formula I wherein A and B have the cis configuration may be prepared by the following reaction scheme:

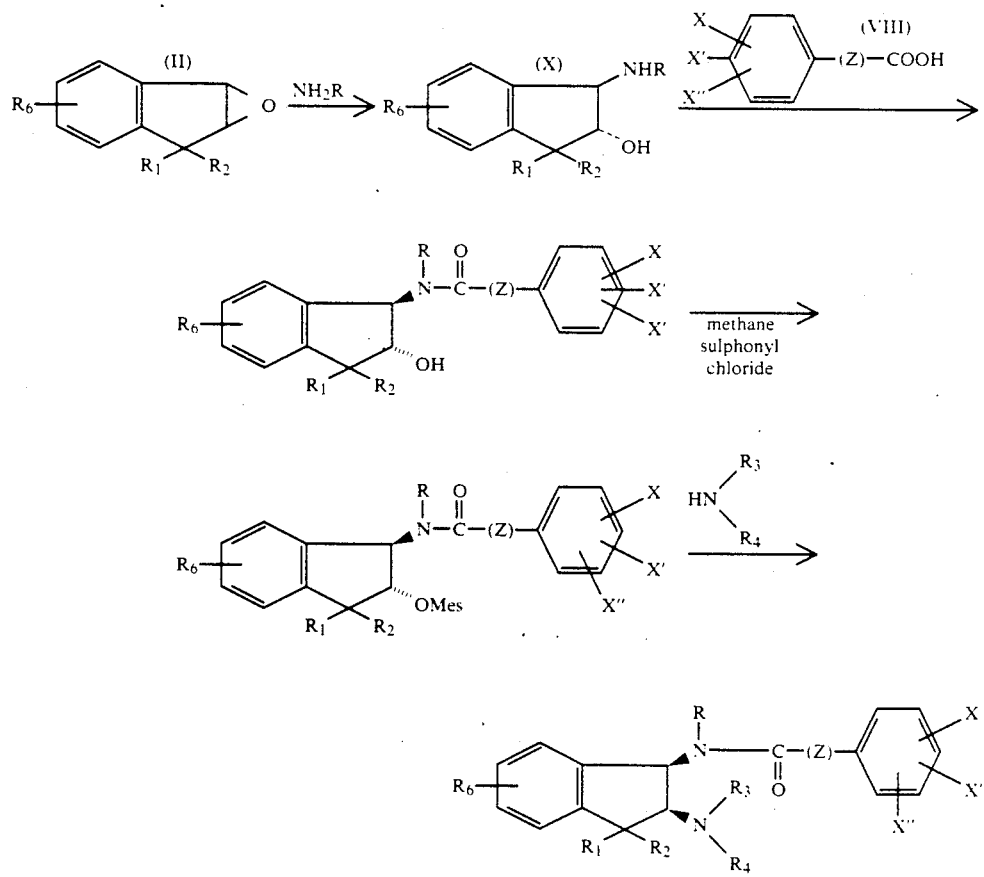

The compounds with the formula (I) as defined above as well as their addition salts with acids show useful pharmacological properties. They show in particular a strong affinity for the opiate receptors and in particular for the K receptors and are endowed with central analgesic properties.

They are also endowed with diuretic properties and anti-arrythmic, anti-cerebral, ischaemic and hypotensive properties.

The novel central analgesic compositions of the invention are comprised of a central analgesically effective amount of at least one compound of formula I and their non-toxic, pharameutically acceptable acid addition salts and an inert pharmaceutical carrier or excipient.

The compositions are useful for the treatment of pain of any origin such as muscular, articular or nervous pain. They are also useful in the treatment of dental pains, migraines, herpes, in the treatment of intense pains, in particular those resistant to peripheral antalgics, for example in the course of a neoplastic process, in the treatment of pancreatitis, nephritic or biliar colics, in the treatment of post-operative and post-traumatic pains.

The subject matter of the invention is also the novel diurectic compositions which comprise at least one compound of formula I and its non-toxic pharmaceutically acceptable acid and addition salts and quaternary ammonium salts and an inert pharmaceutical carrier or excipient.

The compositions may also be used in the treatment of oedematous syndromes, of cardiac insufficiency, of certain obesities, of cirrhoses, in the treatment of severe and refractory oedemas, in particular those from congestive cardiac insufficiency and in the long term treatment of arterial hypertension.

The subject matter of the invention is also the novel anti-arrythmic compositions which comprise at least one compound of formula I and its non-toxic pharmaceutically acceptable acid addition salts and quaternary ammonium salts and an inert pharmaceutical carrier or excipient.

The compositions can be used in the treatment of ventricular, supraventricular and functional arrythmias.

The compositions may be in the form of tablets, dragees, gelules, granules, suppositories, creams, ointments, gels, aerosols and injectable solutions or suspensions.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

Particularly preferred compositions of the invention contain as the active compounds a member of the group consisting of

[trans($\pm$)]3,4-dichloro-N-[2,3-dihydro-2-(1-pyrrolidinyl)-1H-inden-1-yl]-N-methyl-benzene-acetamide,

[trans($\pm$)]N-[2,3-dihydro-2-(1-pyrrolidinyl)-1H-inden-1-yl]-N-methyl-3-nitro-benzene-acetamide,

[trans($\pm$)]N-[2,3-dihydro-2-(1-pyrrolidinyl)-1H-inden-1-yl]-N-methyl-4-nitro-benzene-acetamide,

[trans($\pm$)]N-[2,3-dihydro-2-(1-pyrrolidinyl)-1H-inden-1-yl]-N-methyl-(4-trifluoromethyl)-benzene-acetamide,

[trans($\pm$)]2-(3,4-dichlorophenoxy)-N-[2,3-dihydro-2-(1-pyrrolidinyl)-1H-inden-1-yl]-N-methyl-acetamide,

[trans($\pm$)]3,4-dichloro-N-[2,3-dihydro-2-(dimethylamino)-1H-inden-1-yl]-N-methyl-benzene acetamide and

[trans($\pm$)]N-[2,3-dihydro-2-(1-pyrrolidinyl)-1H-inden-1-yl]-N-methyl-4-nitro-benzene-acetamide (isomer A) and their non-toxic, pharmaceutically acceptable acid addition salts.

The novel method of relieving pain in warm-blooded animals, including humans, comprises administering to warm-blooded animals a central analgesically effective amount of at least one compound of formula I and their non-toxic, pharmaceutically acceptable acid addition salts. The compounds may be administered orally, rectally or parenterally and the usual daily dose is 0.05 to 6 mg/kg depending on the condition treated, the method of administration and the specific compound.

The novel method of inducing diuresis in warm-blooded animals including humans, comprises administering to warm-blooded animals a diuretically effective amount of at least one compound of formula I and its non-toxic, pharmaceutically acceptable acid addition salts and quaternary ammonium salts. The compound may be administered orally rectally or parenterally and the usual daily dose is 1 $\gamma$ to 1 mg/kg depending on the condition treated, the specific compound and method of administration. For example a daily oral dose of 10 to 1 mg/kg and a daily parenteral dose of 1 $\gamma$ to 100 $\gamma$/kg are useful for diuretic activity, more particularly a daily oral dose of 10 $\gamma$ to 100 $\gamma$/kg and a daily parenteral dose 5 $\gamma$ to 50 $\gamma$/kg.

The novel method of treating arrythmia in warm blooded animals including humans, comprises administering to warm-blooded animals a antiarythmically effective amount of at least one compound of formula I and its non-toxic, pharmaceutically acceptable acid addition salts and quaternary ammonium salts. The compounds may be administered preferably orally, rectally or parenterally and the usual daily dose is 1 to 10 mg/kg depending on the condition treated, the specific compound and method of administration.

For example, the daily oral dose for the treatment of ventricular, supraventricular and junctional arrythmias is 1 to 10 mg/kg.

The starting compounds of formula II wherein $R_1$ and $R_2$ are hydrogen or alkyl of 1 to 5 carbon atoms may be prepared by oxidation of the corresponding indene. The other compounds of formula II, especially wherein $R_1$ and $R_2$ form tetrahypropyran may be prepared by the following reaction:

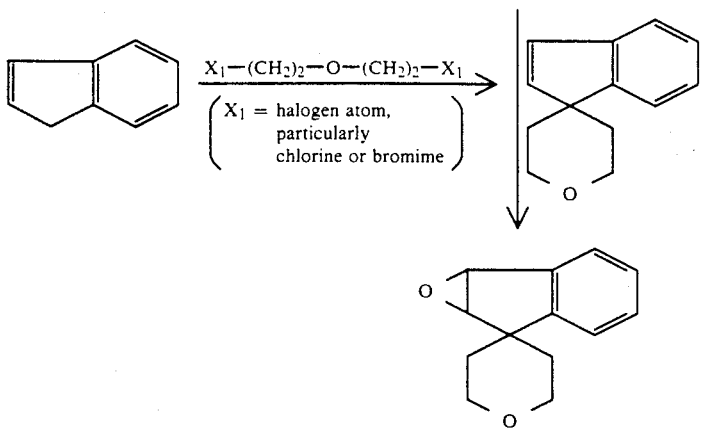

The novel intermediates of the invention are the compounds of formulae IV, VI, VII, IX and XI wherein $R_6$ is other than hydrogen.

In the following examples there are described several preferred embodiments to illustrate the invention. However, it should be understood that the invention is not intended to be limited to the specific embodiments.

EXAMPLE 1

[Trans(±)]3,4-dichloro-N-[2,3-dihydro-2-(1-pyrrolidinyl)-1H-inden-1-yl]-N-methyl-benzene-acetamide and its hydrochloride

STEP A:

[trans(±)]2,3-dihydro-1-(1-pyrrolidinyl)-1H-inden-2-ol 10.8 ml of pyrrolidine in 6.75 g of 2,3-epoxy-indane [described by Mousseron et al. Bulletin de la Societe Chimique de France, 1946, p. 629–630] in 10.8 ml of demineralized water. The temperature rose to 65° C. and the solution was stirred for 90 minutes at this temperature and 20 ml of demineralized water were added when the reaction was finished. Excess pyrrolidine was distilled off under reduced pressure to obtain an oily phase and an aqueous phase. These are saturated with sodium chloride at 20° C. and 1 ml of 32% sodium hydroxide was added. Extraction was done with ether and after drying and concentrating by distilling under reduced pressure, the oil obtained was purified by chromatography over silica (eluent:ethyl acetate with 5% of triethylamine) to obtain 8.31 g of [trans(±)]2,3-dihydro-1-(1-pyrrolidinyl)-1H-inden-2-ol.

STEP B:

[Trans(±)]2,3-dihydro-N-methyl-2-(1-pyrrolidinyl)-1H-inden-1-amine

A mixture of 8.71 g of the product of Step A, 87 ml of methylene chloride and 13.8 ml of triethylamine was cooled to −20° C. and at this temperature a solution of 6.6 ml of methane sulfonyl chloride and 8.7 ml of methylene chloride was added. The mixture was stirred for 20 minutes at −20° C. and then allowed to return to 0° C. and washed with iced water. The wash water was extracted with methylene chloride and the combined organic phases were dried and concentrated to dryness under reduced pressure to obtain 13.36 g of a resin corresponding to the trans(±)methane sulfonate of 2,3-dihydro-2-(1-pyrrolidinyl)-1H-inden-2-ol. The residue was treated in an autoclave with a 35 to 40% aqueous solution of monomethylamine by heating to 80° C. for 20 hours (pressure stabilized at 3 bars). It was then cooled to 20° C., and taken up in 100 ml of ether, saturated with sodium chloride and decanted. The organic phase was washed with saturated salt water, then dried, treated with activated charcoal, filtered. rinsed and concentrated to dryness under reduced pressure to obtain 6.98 g of a resin which was purified by chromatography over silica (eluent:ethyl acetate-methanol-triethylamine 85-10-5) to obtain 3.71 g of [trans(±)]2,3-dihydro-N-methyl-2-(1-pyrrolidinyl)-1H-inden-1-amine.

STEP C:

[Trans(±)]3,4-dichloro-N-[2,3-dihydro-2-(1-pyrrolidinyl)-1H-inden-1-yl]-N-methyl-benzene-acetamide A mixture of 2.66 g of 3,4-dichlorophenylacetic acid, 2.11 g of carbonyldiimidazole and 20 ml of tetrahydrofuran was stirred for 1 hour and then a solution of 2.16 g of the product of Step B in 5 ml of tetrahydrofuran was added slowly. The mixture was stirred for 3 hours 30 minutes and then the tetrahydrofuran was distilled off under reduced pressure. The residue was taken up in 100 ml of ether and after washing with a saturated solution of sodium bicarbonate, then with saturated salted water, drying and concentrating to dryness under reduced pressure, 4.68 g of [Trans(±)]3,4-dichloro-N-[2,3-dihydro-2-(1-pyrrolidinyl)-1H-inden-1-yl]-N-methyl-benzene-acetamide in the form of a base were obtained.

Preparation of the Hydrochloride

The said product was dissolved at 50° C. in 10 ml of 99% ethanol, and to the hot solution, 3 ml of an ethanol solution of anhydrous hydrochloric acid (titer=5.75N) were added. After filtering immediately hot, the filtrate was rinsed with ethanol at 50° C. and crystallization was initiated at 30° C. The mixture stood for 2 hours at 20° C. for crystallization to take place and the crystals were separated, rinsed with ethanol and with ether, dried under reduced pressure to obtain 3.815 g of the expected hydrochloride melting at 242° C.

EXAMPLE 2

[Trans(±)]3,4-dichloro-N-[2,3-dihydro-1-(1-pyrrolidinyl)-1H-inden-2-yl]-N-methyl-benzene-acetamide and its fumarate

STEP A:

[Trans(±)]2,3-dihydro-1-[methyl(benzyl)-amino]-1H-inden-2-ol

A mixture of 10.06 g of 2,3-epoxy-indane, 50 ml of demineralized water and 15 ml of N-methyl-benzylamine was stirred at 95° C. for 1 hour and after cooling to 20° C., 50 g of ice were added. The gum obtained was filtered at 0° to +5° C., rinsed with water and re-dissolved in 250 ml of ethyl acetate. Extraction was done successively with 70 ml, 50 ml, and 30 ml of 2N hydrochloric acid and the aqueous phases were washed with ethyl acetate. 150 ml of ethyl acetate were added to the hydrochloric extracts and the pH was adjusted to 9 to 10 by 25 g of sodium bicarbonate with stirring and 0.5 ml of sodium hydroxide were added. The mixture was decanted, re-extracted with ethyl acetate, washed with salted water, dried, treated with activated charcoal, rinsed, and concentrated to dryness under reduced pressure to obtain 17.29 g of resin which were taken up in 60 ml of n-hexane. Crystallization was initiated at 20° C. and after triturating, separating, rinsing with n-hexane and drying, 15.95 g of [Trans(±)]2,3-dihydro-1-[methyl(benzyl)-amino]-1H-inden-2-ol melting at 64° C. were obtained.

STEP B:

[Trans(±)]1-[2,3-dihydro-2-[methyl-(benzyl)-amino]-1H-inden-1-yl]-pyrrolidine a) A solution of 13.95 g of the product of Step A, 98 ml of methylene chloride and 23 ml of triethylamine was cooled to −20° C. and a solution of 8.5 ml of methanesulfonyl chloride and of methylene chloride was introduced with stirring for 30 minutes at −20° C. The temperature was returned to 0° C. over 5 minutes, and after washing with iced water, drying and concentrating to dryness under reduced pressure, 20.48 g of an oil were obtained corresponding to the methane sulfonate of [trans(±)]2,3-dihydro-1-[methyl-(benzyl)-amino]-1H-inden-2-ol.

b) 20.48 g of the said product were stirred at 85° C. in 60 ml of pyrrolidine and 60 ml of demineralized water and the emulsion was stirred at 65° C. for 90 minutes. Then, the excess pyrrolidine was distilled off under reduced pressure and the residue was taken up in a water-ice mixture. The gum obtained was filtered, rinsed with water and dissolved in ether. The water was decanted and the ethereal solution was dried and concentrated to dryness under reduced pressure to obtain 15.39 g of [Trans(±)]1-[2,3-dihydro-2-[methyl-(benzyl)-amino]-1H-inden-1-yl]-pyrrolidine.

STEP C:

[Trans(±)]1-[2,3-dihydro-2-(methylamino)-1H-inden-1-yl]-pyrrolidine 15.39 g of the product of Step B, 230 ml of methanol, 15.5 ml of hydrochloric acid and 9.25 g of 10% palladium on activated charcoal were mixed together and then hydrogenated for 2 hours 30 minutes with stirring and 1800 mbars pressure of hydrogen. The catalyst and the activated charcoal were filtered off and the filtrate was rinsed with methanol, then concentrated under reduced pressure to obtain an oil. Ether was added with stirring, followed by alkalinization with 15 ml of 32% sodium hydroxide while maintaining the temperature at 20° C. Then, after stirring, decanting, re-extracting the aqueous phase with ether, drying the organic phases and concentrating to dryness under reduced pressure, 9.85 g of [Trans(±)]1-[2,3-dihydro-2-(methylamino)-1H-inden-1-yl]-pyrrolidine were obtained.

STEP D:

[Trans(±)]3,4-dichloro-N-[2,3-dihydro-1-(pyrrolidinyl)-1H-inden-2-yl]-n-methyl-benzene-acetamide A mixture of 2.66 g of 3,4-dichlorophenyl-acetic acid, 2.10 g of carbonyl-diimidazole and 25 ml of tetrahydrofuran was stirred for 1 hour at 20° to 25° C. and then 2.16 g of the product of Step C was added in 10 ml of tetrahydrofuran with stirring for 3 hours 30 minutes at 20° to 25° C. after which the tetrahydrofuran was distilled off under reduced pressure. The residue was taken up in ether, washed with a saturated solution of sodium bicarbonate and then with water saturated with sodium chloride. After drying and concentrating to dryness under reduced pressure, 5.048 g of [Trans(±)]3,4-dichloro-N-[2,3-dihydro-1-(pyrrolidinyl)-1H-inden-2-yl]-n-methyl-benzene-acetamide as a fluid resin.

Preparation of the Fumarate

The crude base was dissolved in 50 ml of 99% ethanol, then filtered and rinsed with ethanol, 1.25 g of fumaric acid were added with heating to dissolve it and the salt crystallized out on cooling and was separated, rinsed with 99% ethanol, then with ether, dried at 65° C. under reduced pressure to obtain 4.908 g of the fumarate which was crystallized first from isopropanol with 5% of water, then from 99% ethanol for 4.038 g of the expected product melting at 140° C.

EXAMPLE 3

[Trans(±)]3,4-dichloro-N-[2.2',3,3',5',6'-hexahydro-2-(1-pyrrolidinyl)-spiro[1H-inden-1.4'-(4H)-pyran]-3-yl-N-methyl-benzene-acetamide and its hydrochloride

STEP A:

2,3,5,6-tetrahydro-spiro-pyran-4-(4H)-1'-indene 250 ml of tetrahydrofuran and 250 ml of hexamethyl-phosphorotriamide were added to 53 g of 50% sodium hydride in oil previously washed with petroleum ether and then without exceeding 0° C., 58 g of indene in 50 ml of tetrahydrofuran were added. The temperature was allowed to rise to 15° C., and over 30 minutes at 16° C.±1°, 71.55 g of β-chloroethyl ether in 50 ml of tetrahydrofuran were added with stirring. Stirring was continued for another 90 minutes and then the mixture was carefully poured into 1 liter of 2N hydrochloric acid containing about 500 g of ice. Extraction was done with isopropyl ether, and the extracts were washed with water, dried, and stirred with animal charcoal and with alumina. After separating and concentrating to dryness under reduced pressure, 100 g of oil were obtained which was taken up in 200 ml of petroleum ether. Crystallization was initiated with icing for 3 hours and then the crystals were separated, washed with iced petroleum ether to obtain 55 g of 2,3,5,6-tetrahydro-spiro pyran-4-(4H)-1'-indene. The mother liquor were evaporated to dryness and the residue was taken up in 40 ml of methylene chloride, chromatographed on silica to obtain 25 g of product which was crystallized from petroleum ether to obtain 14 g of 2,3,5,6-tetrahydro-spiro-pyran-4-(4H)-1'-indene melting at 83° C.

STEP B:
2',3'-epoxy-2,3,5,6-tetrahydro-spiro-[pyran-4-(4H)-1'-indane]

At 15° C., 6.3 g of m-chloroperbenzoic acid were added to 5.58 g of the product of Step A in 60 ml of methylene chloride and the mixture was cooled slightly so as not to exceed 30° C. After half-an-hour, the m-chlorobenzoic acid crystallized and the mixture stood for 1 hour. Then, it was poured into a mixture of water and sodium bicarbonate, extracted with methylene chloride, washed with a sodium bicarbonate solution, dried and concentrated to dryness. The residue was crystallized from methylene chloride and isopropyl ether. After separating, washing with isopropyl ether and drying at 80° C., 4.23 g of 2',3'-epoxy-2,3,5,6-tetrahydro-spiro-[pyran-4-(4H)-1'-indane] melting at 157° C. were obtained.

STEP C:
[Trans(±)]2,2',3,3',5',6'-hexanhydro-3-(1-pyrrolidinyl)-spiro-[1H-inden-1,4'-(4H)-pyran]-2-ol 11.66 g of the product of Step B in 10 ml of demineralized water and 12.6 ml of pyrrolidine were heated to 60° to 70° C., then to 50° C. while stirring for 15 minutes, followed by cooling to 30° C., diluting with 100 ml of iced water, filtering, and rinsing the gum obtained with water. The gum was taken up in ether and the water was decanted. After drying and concentrating to dryness under reduced pressure, 12.8 g of [Trans(±)]2,2',3,3',5',6'-hexahydro-3-(1-pyrrolidinyl)-spiro-[1H-inden-1,4'-(4H)-pyran]-2-ol were obtained. The aqueous mother liquors were extracted with ether, dried, concentrated to dryness under reduced pressure, and 3.63 g of the expected product were recovered.

Preparation of the Hydrochloride

The 16.43 g of product obtained were dissolved in 15 ml of ethanol and then 11 ml of an ethanol solution of hydrochloric acid (5.75N) were added. The hydrochloride crystallized out and the suspension was diluted slowly with stirring with 55 ml of ether, then separated, rinsed with an ethanol-ether mixture, then with ether and dried under reduced pressure at 60° to 65° C. to obtain 13.65 g of the hydrochloride melting at 183° C.

STEP D: Methane sulfonate of [trans(±)]2,2',3,3',5',6'-hexahydro-3-(1-pyrrolidinyl)-spiro-[1H-inden-1,4'-(4H)-pyran]-2-ol 9.25 ml of triethylamine were introduced into a solution of 6.19 g of the product of Step C in 40 ml of methylene chloride which was cooled to −15° C. and a solution of 3.1 ml of methane sulfonyl chloride (0.04M) in 20 ml of methylene chloride was added with stirring for 30 minutes at −15° C.±2°. The temperature was returned to 0° C. and the reaction medium was poured into 100 ml of water at +10° C. After decanting, extracting with methylene chloride, washing with water, drying, adding silica, stirring for 5 minutes, filtering, rinsing and concentrating to dryness under reduced pressure, 7.45 g of an oil were obtained. The oil was dissolved in 30 ml of ether at 20° C. and crystallization was initiated. The crystals were separated, rinsed with ether, and dried under reduced pressure to obtain 5.15 g of methane sulfonate of [trans(±)]2,2',3,3',5',6'-hexahydro-3-(1-pyrrolidinyl)-spiro-[1H-inden-1,4'-(4H)-pyran]-2-ol melting at 136° to 137° C.

STEP E:
[Trans(±)]2,2',3,3',5',6'-hexahydro-N-methyl-2-(1-pyrrolidinyl)-spiro-[1H-inden-1,4'-(4H)-pyran]-3-amine A mixture of 4.65 g of the product of Step D and 9.3 ml of a 35 to 40% aqueous solution of methylamine was stirred at 70° C. for 18 hours 30 minutes in an autoclave and the pressure stabilized at 1.2-1.4 bar. After cooling, the mixture was taken up in 20 ml of saturated salt water and 100 ml of ether with stirring to dissolve the gum. Then the mixture was decanted, extracted with ether, washed with salted water, dried and concentrated to dryness under reduced pressure to obtain a thick oil which was dissolved in 10 ml of n-hexane at 40° C. Crystallization was initiated and the crystals were separated at 0°−+5° C., rinsed with n-hexane, dried under reduced pressure to obtain 3.26 g of [Trans(±)]2,2',3,3',5',6'-hexahydro-N-methyl-2-(1-pyrrolidinyl)spiro[1H-inden-1,4'-(4H)-pyran]-3-amine melting at 88° C.

Preparation of the Dihydrochloride 2.18 g of the product were suspended in 7 ml of ethanol and 3.5 ml of ethanol containing anhydrous hydrochloric acid (5.75N) were added at 20° C. After filtering, 10 ml of ether were added slowly to the filtrate and the crystals obtained were separated, rinsed with an ethanol-ether mixture and with ether, then dried under reduced pressure at 60° to 65° C. to obtain 2.74 g of the dihydrochloride melting at 270° C.

STEP F:
[Trans(±)]3,4-dichloro-N-[2,2',3,3',5',6'-hexahydro-2-(1-pyrrolidinyl)spiro[1H-inden-1,4'-(4H)-pyran]-3-yl-N-methyl-benzene-acetamide Using the procedure of Step C of Example 1, 789 mg of 3,4-dichlorophenylacetic acid in 10 ml of tetrahydrofuran and 624 mg of carbonyldiimidazole and 1 g of the product (base) of Step E were reacted to obtain 1.443 g of [Trans(±)]3,4-dichloro-N-[2,2',3,3',5',6'-hexahydro-2-(1-pyrrolidinyl)spiro[1H-inden-1,4'-(4H)-pyran]3-yl-N-methyl-benzene-acetamide melting at 131° C. after purification with n-hexane.

Preparation of the Hydrochloride 0.5 g of base were dissolved in 3 ml of ethanol at reflux and the solution was filtered hot and rinsed with boiling ethanol. 0.4 ml of a solution in ethanol of anhydrous hydrochloric acid (5.75N) were added to the filtrate and after separating, rinsing with 100% ethanol and with ether and drying under reduced pressure at 60° to 65° C., 504 mg of hydrochloride melting at 230° C. were obtained.

EXAMPLE 4
(E) butenedioate of [trans(±)]3,4-dichloro-N-[2,2',3,3',5',6'-hexahydro-3-(1-pyrrolidinyl)-spiro(1H-inden-1,4'-(4H)-pyran)-2-yl]-N-methyl-benzene-acetamide

STEP A:
[Trans(±)]2,2',3,3',5',6'-hexahydro-3-[methyl-(benzyl)-amino]spiro[1H-inden-1,4'-(4H)-pyran]-2-ol Using the procedure of Step A of Example 2, 10.1 g of 2,3'-epoxy-2,3,5,6-tetrahydrospiro-pyran-4-(4H)-1'-indane in 10 ml of methylbenzylamine and 50 ml of demineralized water was reacted to obtain 12.79 g of [trans(±)]2,2',3,3',5',6'-hexahydro-3-[methyl-(benzyl)- amino]-spiro-(1H-inden-1,4'-(4H)-pyran]-2-ol which was used as is for the following part of the synthesis.

Preparation of the Hydrochloride 4.40 g of the said base were dissolved in 15 ml of 100% ethanol at 20° C. and the solution was filtered. 4 ml of an ethanol solution of anhydrous hydrochloric acid (5.75N) were added to it, followed by dilution with 24 ml of ether at 20° C. Crystallization was initiated at 20° C. and 24 ml of ether were added. The crystals were separated at 20° C., rinsed with an ethanol-ether mixture, then with ether, dried under reduced pressure at 60° to 65° C. to obtain 4.2 g of the hydrochloride melting at 192° C.

STEP B: Methane sulfonate of [trans(±) 2,2',3,3',5',6'-hexahydro-3-[methyl(benzyl)-amino]-spiro-[1H-inden-1,4'-(4H)-pyran]-2-ol Using the procedure of Step B of Example 2, 12.79 g of the product of Step A in 100 ml of methylene chloride, 16.5 ml of triethylamine, and 6.1 ml of methane sulfonyl chloride in 30 ml of methylene chloride were reacted to obtain 16.07 g of methane sulfonate of [trans(±) 2,2',3,3',5',6'-hexahydro-3-[methyl(benzyl)-amino]-spiro[1H-inden-1,4'-(4H)-pyran]-2-ol.

STEP C: [Trans(±)]2,2',3,3',5',6'-hexahydro-N-methyl-N-(benzyl)-3-(1-pyrrolidinyl)-spiro[1H-inden-1,4'-(4H)-pyran]-2-amine Using the procedure of b) of Step B of Example 2, the 16.07 g of the product of Step B, 37 ml of pyrrolidine and 37 ml of demineralized water were reacted to obtain 14.16 g of [Trans(±)]2,2',3,3',5',6'-hexahydro-N-methyl-N-(benzyl)-3-(1-pyrrolidinyl)-spiro[1H-inden-1,4'-(4H)-pyran]-2-amine which was used as is for the remainder of the synthesis.

Preparation of the Hydrochloride 2.60 g of said base were dissolved with warming in 6.5 ml of isopropanol and at 20° C. 4 ml of anhydrous (4.4N) hydrochloric acid in isopropanol were added. After filtering and rinsing with isopropanol, 42 ml of ether were added to the filtrate. The gum was separated, rinsed with ether, dried under reduced pressure at 62° to 65° C. to obtain 2.82 g of the hydrochloride melting at 150° C.

STEP D: Dihydrochloride of [trans(±)]2,2',3,3',5',6'-hexahydro-N-methyl-3-(1-pyrrolidinyl)-spiro[1H-inden-1,4'-(4H)-pyran]-2-amine Using the procedure of Step C of Example 2, 12.35 g of crude base of Step C, 247 ml of methanol and 17.3 ml of hydrochloric acid and 7.4 g of 10% palladium on activated charcoal were subjected to hydrogenation at 24° to 26° C. under 1800 mbars for about 1 hour. At the end of the reaction, the activated charcoal and the catalyst were filtered off under nitrogen, followed by rinsing with methanol and concentrating the filtrate under reduced pressure. The residue was dissolved at 20° C. in 60 ml of isopropanol, and after initiating crystallization at 20° C., the solution stood at ambient temperature for 2 hours. The crystals were separated, rinsed with isopropanol, then with ether and dried under reduced pressure at 65° C. to obtain 8.80 g of crude product. 5.48 g of the said product were dissolved in 20 ml of methanol, filtered, rinsed with methanol, concentrated under reduced pressure, taken up in isopropanol and dissolved by warming. After filtering hot, and rinsing with boiling isopropanol, crystallization was initiated and the crystals were separated, rinsed with isopropanol and with ether and dried under reduced pressure to obtain 5.16 g of the anhydrous dihydrochloride of [trans(±)]2,2',3,3',5',6'-hexahydro-N-methyl-3-(1-pyrrolidinyl)-spiro[1H-inden-1,4'-(4H)-pyran]-2-amine in the form of the dihydrochloride melting at 235° C. of the hydrated hydrochloride.

STEP E: (E) butenedioate of [trans(±)]3,4-dichloro-N-[2,2',3,3',5',6'-hexahydro-3-(1-pyrrolidinyl)-spiro[1H-inden-1,4'-(4H)-pyran]-2-yl]-N-methyl-benzene-acetamide Using the procedure of Step D of Example 2, 2.05 g of 3,4-dichlorophenylacetic acid, 20 ml of tetrahydrofuran, 1.62 g of carbonyldiimidazole, 2.6 ml of triethylamine and 3.27 g of the product of Step D were reacted to obtain 4.61 g of (E) butenedioate of [trans(±) 3,4-dichloro-N-[2,2',3,3',5',6'-hexahydro-3-(1-pyrrolidinyl)-spiro[1H-inden-1,4'-(4H)-pyran]-2-yl]-N-methyl-benzene-acetamide. 4.456 g of the product were purified by chromatography on silica (eluent:methylene chloride-ethyl acetate 1-1). The solvent was eliminated to obtain 3.71 g of pure product.

Obtaining the Fumarate 3.474 g of the purified base were dissolved in 15 ml of ethanol and 941 mg of fumaric acid were added with heating to obtain a solution. The solution was filtered hot and rinsed with boiling ethanol. The filtrate crystallized hot and the crystals were separated at 20° C. rinsed with ethanol and with ether and dried under reduced pressure at 60° to 65° C. to obtain 3.631 g of the fumarate melting at 152° C.

Using the procedure of Step C of Example 1, the [trans(±)]2,3-dihydro-N-methyl-2-(1-pyrrolidinyl)-1H-inden-1-amine of Step B of Example 1 and the corresponding acid were reacted to obtain the products of Example 5 to 14.

EXAMPLE 5

[Trans(±)]N-[2,3-dihydro-2-(1-pyrrolidinyl)-1H-inden-1-yl]-N-methyl-4-(trifluoromethyl)-benzene-acetamide and its hydrochloride By using 0.645 g of the product of Step B of Example 1 and 0.796 g of 4-trifluoromethylphenyl acetic acid, 0.673 g of the expected hydrochloride melting at 245° C. were obtain.

Analysis: $C_{23}H_{25}F_3N_2O$, HCl: 438.923.

| Calculated: | % C 62.94 | % H 5.97 | % N 6.38 | % F 12.99 | % Cl 8.08 |
|---|---|---|---|---|---|
| Found: | 62.7 | 6.2 | 6.1 | 12.9 | 7.2 |

EXAMPLE 6

[Trans(±)]N-[2,3-dihydro-2-(1-pyrrolidinyl)-1H-inden-1-yl]-N-methyl-3-(trifluoromethyl)-benzene-acetamide and its hydrochloride By using 0.432 g of the product of Step B of Example 1 and 0.530 g of m-trifluoromethylphenyl acetic acid, 0.786 g of [trans(±)]N-[2,3-dihydro-2-(1-pyrrolidinyl)-1H-inden-1-yl]-N-methyl-3-(trifluoromethyl)-benzene-acetamide, then 0.606 g of the expected hydrochloride melting at about 211° C. (decompose) were obtained.

Analysis: $C_{23}H_{25}F_3N_2O$, HCl: 438.923.

| Calculated: | % C 62.94 | % H 5.97 | % N 6.38 | % F 12.99 | % Cl 8.08 |
|---|---|---|---|---|---|
| Found: | 62.8 | 6.1 | 6.3 | 13.0 | 8.2 |

EXAMPLE 7

[Trans(±)]N-[2,3-dihydro-2-(1-pyrrolidinyl)-1H-inden-1-yl]-N-methyl-2-(trifluoromethyl)-benzene-acetamide and its hydrochloride By using 0.432 g of the products of Step B of Example 1 and 0.530 g of 0-trifluoromethylphenyl acetic acid, 0.945 g of [trans(±)]N-[2,3-dihydro-2-(1-pyrrolidinyl)-1H-inden-1-yl]-N-methyl-2-(trifluoromethyl)-benzene-acetamide and its hydrochloride, then 0.751 g of the expected hydrochloride melting at about 260° C. (decompses) were obtained.

Analysis: $C_{23}H_{25}F_3N_2O$, HCl: 438.923.

| Calculated: | % C 62.94 | % H 5.97 | % N 6.38 | % F 12.99 | % Cl 8.08 |
|---|---|---|---|---|---|
| Found: | 62.6 | 6.0 | 6.1 | 13.3 | 8.4 |

EXAMPLE 8

[Trans(±)]N-[2,3-dihydro-2-(1-pyrrolidinyl)-1H-inden-1-yl]-N-methyl-4-nitro-benzene-acetamide and its hydrochloride By using 1.73 g of the product of Step B of Example 1 and 1.88 g of p-nitrophenyl acetic acid, 3.7 g of [trans(±)]N-2,3-dihydro-2-(1-pyrrolidinyl)-1H-inden-1-yl]-N-methyl-4-nitro-benzene-acetamide and————then 0.33 g of the expected hydrochloride melting at 236° C. were obtained.

Analysis: $C_{22}H_{25}N_3O_3$, HCl: 415.923.

| Calculated: | % C 63.53 | % H 6.30 | % N 10.10 | % Cl 8.53 |
|---|---|---|---|---|
| Found: | 63.4 | 6.2 | 9.9 | 8.6 |

EXAMPLE 9

[Trans(±)]N-[2,3-dihydro-2-(1-pyrrolidinyl)-1H-inden-1-yl]-N-methyl-3-nitro-benzene-acetamide and its hydrochloride By using 0.432 g of the product of Step B of Example 1 and 0.471 g of m-nitrophenyl acetic acid, 0.838 g of [trans(±)]N-[2,3-dihydro-2-(1-pyrrolidinyl)-1H-inden-1-yl]-N-methyl-3-nitro-benzene-acetamide————then 0.58 g of the expected hydrochloride melting at about 160° C. were obtained.

Analysis: $C_{22}H_{25}N_3O_3$, HCl: 415.923.

| Calculated: | % C 63.53 | % H 6.30 | % N 10.10 | % Cl 8.53 |
|---|---|---|---|---|
| Found: | 63.6 | 6.4 | 10.1 | 8.5 |

EXAMPLE 10

[Trans(±)]N-[2,3-dihydro-2-(1-pyrrolidinyl)-1H-inden-1-yl]-N-methyl-2-nitro-benzene-acetamide and its hydrochloride By using 0.432 g of the product of Step B of Example 1 and 0.471 g of o-nitrophenyl acetic acid, 0.492 g of [trans(±)]N-[2,3-dihydro-2-(1-pyrrolidinyl)-1H-inden-1-yl]-N-methyl-2-nitro-benzene-acetamide hydrochloride melting at about 215° C. were obtained.

Analysis: $C_{22}H_{25}N_3O_3$, HCl: 415.923.

| Calculated: | % C 63.53 | % H 6.30 | % N 10.10 | % Cl 8.53 |
|---|---|---|---|---|
| Found: | 63.6 | 6.4 | 10.1 | 8.5 |

EXAMPLE 11

[Trans(±)]N-[2,3-dihydro-2-(1-pyrrolidinyl)-1H-inden-1-yl]-N-methyl-3,4,5-trimethoxy-benzene-acetamide and its hydrochloride By using 0.432 g of the product of Step B of Example 1 and 0.588 g of 3,4,5-trimethoxyphenyl acetic acid, 1.070 g of [Trans(±)]N-[2,3-dihydro-2-(1-pyrrolidinyl)-1H-inden-1-yl]-N-methyl-3,4,5,-trimethoxy-benzene-acetamide and then 0.789 g of its hydrochloride melting at 217° C. were obtained.

Analysis: $C_{25}H_{32}H_2N_4O$, HCl: 461.006.

| Calculated: | % C 65.13 | % H 7.21 | % N 16.08 | % Cl 7.69 |
|---|---|---|---|---|
| Found: | 65.0 | 7.3 | 15.9 | 7.4 |

EXAMPLE 12

[Trans(±)]N-[2,3-dihydro-2-(1-pyrrolidinyl)-1H-inden-1-yl]-4-N-dimethyl-benzene-acetamide and its hydrochloride By using 0.650 g of the product of Step B of Example 1 and 0.586 g of para-tolyl acetic acid, 1.10 g of [trans(±)]N-[2,3-dihydro-2-(1-pyrrolidinyl)-1H-inden-1-yl]-4-N-dimethyl-benzene-acetamide and then 0.665 g of its hydrochloride melting at 212° C. were obtained.

Analysis: $C_{23}H_{28}N_2O$, HCl: 384.948.

| Calculated: | % C 71.76 | % H 7.50 | % N 7.28 | % C 9.21 |
|---|---|---|---|---|
| Found: | 71.8 | 7.6 | 7.1 | 9.2 |

EXAMPLE 13

[Trans(±)]N-[2.3-dihydro-2-(1-pyrrolidinyl)-1H-inden-1-yl]-3,4-dimethoxy-N-methyl-benzene-acetamide and its fumarate By using 0.650 g of the product of Step B of Example 1 and 0.765 g of 3,4-dimethoxyphenyl acetic acid, 1.14 g of [trans(±)]N-[2,3-dihydro-2-(1-pyrrolidinyl)-1H- inden-1-yl]-3,4-dimethoxy-N-methyl-benzene-acetamide————were obtained. To 1 g of this product, there was added 0.35 g of fumaric acid in 7 ml of ethanol, and after filtering, 0.886 g of the expected salt melting at 186° C. were obtained.

Analysis: $C_{24}H_{30}N_2O_3C_4H_4O_4$: 510.583.

| | | | |
|---|---|---|---|
| Calculated: | % C 65.87 | % H 6.71 | % N 5.49 |
| Found: | 66.1 | 6.4 | 5.3 |

EXAMPLE 14

[trans(±)]2-(3,4-dichlorophenoxy)-N-[2,3-dihydro-2-(1-pyrrolidinyl)-1H-inden-1-yl]-N-methyl-acetamide and its hydrochloride By using 0.432 g of the product of Step B of Example 1 and 0.575 g of 3,4-dichlorophenoxy acetic acid, 0.790 g of [trans(±)]2-(3,4-dichlorophenoxy)-N-(2,3-dihydro-2-(1-pyrrolidinyl)-1H-inden-1-yl]-N-methyl-acetamide————and then 0.687 g of the hydrochloride melting at 196° C. were obtained.

Analysis: $C_{22}H_{24}N_2O_2$, HCl: 455.815.

| | | | | |
|---|---|---|---|---|
| Calculated: | % C 57.07 | % H 5.53 | % N 6.14 | % Cl 23.33 |
| Found: | 58.0 | 5.5 | 6.2 | 23.0 |

EXAMPLE 15

[Trans(±)]3,4-dichloro-N-[2,3-dihydro-2-(1-pyrrolidinyl)-1H-inden-1-yl]-N-methyl-benzamide and its hydrochloride 0.670 g of 3,4-dichlorobenzoic acid in ether were added to 0.650 g of the product of Step A of Example 1 in ether with stirring for 16 hours at ambient temperature. Then the mixture was poured into iced water and the ethereal phase was separated by decanting, washed with a saturated aqueous solution of sodium bicarbonate and then with salted water, extracted with ether, dried, and the solvents were elminated under reduced pressure to obtain 1.2 g of the expected product in the form of the base. 1.1 g of the base were dissolved in 25 ml of ethanol and 0.8 ml of an ethanol solution of hydrogen chloride (5.75N) were added to obtain 1.05 g of the hydrochloride.

Analysis: $C_{21}H_{22}Cl_2N_2O$, HCl: 425.789.

| | | | | |
|---|---|---|---|---|
| Calculated: | % C 59.24 | % H 5.44 | % N 6.58 | % Cl 24.98 |
| Found: | 59.0 | 5.5 | 6.6 | 24.7 |

EXAMPLE 16

[Trans(±)]N-[2,3-dihydro-2-(1-pyrrolidinyl)-1H-inden-1-yl]-N-methyl-4-nitro-benzene-acetamide (isomer A) and its hydrochloride

STEP A: Resolution of trans(±)2,3-dihydro-N-methyl-2-(1-pyrrolidinyl)-1H-inden-1-amine

Isomer A 12.1 g of D (+) di-p-tolyl tartaric acid in solution in 22.5 ml of methanol were added to a solution of 6.48 g of the product of Step B of Example 1 in 7.5 ml of methanol, and the mixture was kept in contact for 4 hours at +4° C. After separating, 5.293 g of isomer A salt were collected after crystallizing again from methanol. The melting point was about 170° to 178° C. and the specific rotation was $[\alpha]_D^{20} = +97.5° \pm 5°$ (c=0.26% $H_2$).

The isomer A salt was taken up in 40 ml of sodium hydroxide and the aqueous phase was separated by decanting and then saturated with sodium chloride and extracted with ether. The ether phase was then dried and the solvent was eliminated under reduced pressure to obtain 1.852 g of isomer A in the base form melting at <50° C. and having a specific rotation of $[\alpha]_D^{20} = -10.5° \pm 1°$ (c=1% in $CH_3OH$).

Isomer B

The methanol collected after filtering the above isomer A salt was concentrated to dryness and the residue was taken up in water, ether and sodium hydroxide as above and after extracting with ether and elimination of the solvent, 4.1 g of base were obtained which was dissolved in 6 ml of methanol. A solution of 7.68 g of L(−) di-p-tolyl tartaric acid in 20 ml of methanol was added and crystallization was initiated. The solution stood for 4 hours and after separating and crystallizing from methanol, 3.208 g of the isomer B salt melting at about 117° C. and having a specific rotation of $[\alpha]_D^{20} = -19.5° \pm 2°$ (c=0.5% DMF) were obtained.

The isomer B salt was taken up in water and ether and sodium hydroxide was added as above. After extraction with ether and elimination of the solvent under reduced pressure, 1.117 g of isomer B were obtained in the form of a base melting at >50° C. and having a specific rotation of $[\alpha]_D^{20} = +10.5° \pm 1.5°$ (c=1% $CH_3OH$).

STEP B

Using the procedure of Step C of Example 1, 0.649 g of isomer A in the form of the base of Step A and 0.707 g of p-nitrophenyl acetic acid were reacted to obtain 1.361 g of the expected product in the form of the base, then 0.957 g of the hydrochloride melting about 238° C. and having a specific rotation of $[\alpha]_D^{20} = +85° \pm 1.5°$ (c=1% $H_2O$)

Analysis: $C_{22}H_{25}N_3O_3$, HCl: 415.923.

| | | | | |
|---|---|---|---|---|
| Calculated: | % C 63.53 | % H 6.30 | % N 10.10 | % Cl 8.53 |
| Found: | 63.4 | 6.3 | 10.1 | 8.5 |

EXAMPLE 17

N-[2,3-dihydro-2-(1-pyrrolidinyl)-1H-inden-1-yl]-N-methyl-4-nitro-benzene-acetamide (isomer B) and its hydrochloride Using the procedure of Step C of Example 1, 0.649 g of isomer B in the form of the base of Step A of Example 16 and 0.707 g of p-nitrophenol acetic acid were reacted to obtain 1.369 g of N-[2,3-dihydro-2-(1-pyrrolidinyl)-1H-inden-1-yl]-N-methyl-4-nitro-benzene-acetamide (isomer B) and its hydrochloride in the form of the base, then 0.982 g of hydrochloride melting at about 238° C. and having a specific rotation of $[\alpha]_D^{20} = -80° \pm 1.5°$ (c=1% $H_2O$).

Analysis: $C_{22}H_{25}N_3O_3$ HCl: 415.923.

| | | | | |
|---|---|---|---|---|
| Calculated: | % C 63.53 | % H 6.30 | % N 10.10 | % Cl 8.53 |
| Found: | 63.5 | 6.3 | 10.2 | 8.7 |

EXAMPLE 18

[Trans(±)]-N-[2,3-dihydro-2-(1-pyrrolidinyl)-1H-inden-1-yl]-2,4-dinitro-N-methyl-benzene-acetamide and its hydrochloride STEP A: Oxalate of [trans(±)]2,3-dihydro-N-methyl-2-(1-pyrrolidinyl)-1H-inden-1-amine 1.94 g of the product of Step B of Example 1 were dissolved in 2 ml of ethanol and 1.35 g of dihydrated oxalic acid were added at 50° C. After cooling, separating and rinsing with ethanol, then with ether, 2.3 g of crude product were obtained which was crystallized from methanol with 5% of water to obtain oxalate of [trans(±)]2,3-dihydro-N-methyl-2-(1-pyrrolidinyl)-1H-inden-1-amine melting at 215° C.

Analysis:

| Calculated: | % C 58.11 | % H 6.60 | % N 7.97 |
|---|---|---|---|
| Found: | 58.0 | 6.7 | 7.7 |

STEP B:
[Trans(±)]N-[2,3-dihydro-2-(1-pyrrolidinyl)-1H-inden-1-yl]-2,4-dinitro-N-methyl-benzene-acetamide and its hydrochloride Using the procedure of Step C of Example 1, 0.703 g of the oxalate of Step A and 0.588 g of 2,4-dinitrophenyl acetic acid were reacted to obtain 0.81 g of crude product which was chromatographed over silica (eluent: ethyl acetate, then ethyl acetate with 5% of triethylamine) to obtain 0.359 g of [trans(±)]N-[2,3-dihydro-2-(1-pyrrolidinyl)-1H-inden-1-yl]-2,4-dinitro-N-methyl-benzene-acetamide in base form, then 0.332 g of the hydrochloride melting at 260° C. (decomposes).

Analysis: $C_{22}H_{24}N_4O_5$ HCl: 460.92.

| Calculated: | % C 57.32 | % H 5.47 | % N 12.16 | % Cl 7.69 |
|---|---|---|---|---|
| Found: | 57.4 | 5.5 | 12.0 | 8.0 |

EXAMPLE 19

[Trans(±)]3,5-bis-(trifluoromethyl)-N-[2,3-dihydro-2-(1-pyrrolidinyl)-1H-inden-1-yl]N-methyl-benzene-acetamide and its hydrochloride Using the procedure of Step C of Example 1, 0.432 g of the product of Step B of Example 1 and 3,5-bis-trifluoromethyl-phenyl acetic acid were reacted to obtain the expected hydrochloride (yield of 68%) melting at about 226° C. (decomposes).

Analysis:

| Calculated: | % C 58.86 | % H 4.97 | % N 5.52 | % F 22.49 | % Cl 6.99 |
|---|---|---|---|---|---|
| Found: | 57.0 | 5.0 | 5.5 | 22.8 | 7.2 |

EXAMPLE 20

[Trans(±)]N-[2,3-dihydro-2-(1-pyrrolidinyl)-1H-inden-1-yl]-N-methyl-3,4,5-trimethoxy-benzamide and its hydrochloride At ambient temperature, 1 g of the oxalate of Step A of Example 18 and 0.9 ml of triethylamine were mixed together in tetrahydrofuran and 0.515 g of 3,4,5-trimethoxy-benzoic acid in 5 ml of tetrahydrofuran were added. The mixture was stirred for 16 hours and then poured into 30 ml of iced water and decanted. The organic phase was washed with an aqueous solution of sodium bicarbonate, then with salted water and extracted with ether. The extracts were dried and the solvents were eliminated under reduced pressure to obtain 0.457 g of the expected product in the base form melting at 174° C. The latter was dissolved in 1 ml of an ethanol solution of hydrogen chloride (about 1.68N) and the solvents were eliminated under reduced pressure. The residue was taken up in 5 ml of ether and crystallization was initiated. The expected hydrochloride was separated and dried at 80° C. under reduced pressure and melted at about 210° C.

Analysis: $C_{24}H_{30}N_2O_4$: 446.979.

| Calculated: | % C 64.49 | % H 6.99 | % N 6.27 | % Cl 7.93 |
|---|---|---|---|---|
| Found | 64.7 | 7.0 | 6.2 | 8.2 |

EXAMPLE 21

[Trans(±)]3-(aminosulfonyl)-4-chloro-N-[2,3-dihydro-2-(1-pyrrolidinyl)-1H-inden-1-yl]-N-methyl benzamide and its hydrochloride Using the procedure of Example 20, 0.907 g of the product of Step B of Example 1 and with 4-chloro-3-amino-sulfonyl benzoic acid chloride were reacted to obtain the expected hydrochloride (yield of 66%) melting at >260° C.

Analysis:

| Calculated: | % C 53.62 | % H 5.35 | % N 8.93 | % S 6.82 | % Cl 15.07 |
|---|---|---|---|---|---|
| Found: | 53.4 | 5.6 | 8.6 | 6.7 | 14.8 |

The 4-chloro-3-aminosulfonyl benzoic acid chloride used at the start of the Example was prepared as follows:

1 g of 3-sulfonyl-4-chloro benzoic acid were heated at reflux with stirring for 2 hours and excess thionyl chloride was eliminated under reduced pressure to obtain 1.098 g of the expected product melting at 158° C.

EXAMPLE 22

[Trans(±)]3,4-dichloro-N-[2,3-dihydro-2-(1-pyrrolidinyl)-1H-inden-1-yl]-N-α-dimethyl-benzene-acetamide isomer A and isomer B and their hydrochloride A mixture of 2.30 g of α-methyl-3,4-dichlorophenyl acetic acid, 1.73 g of the product of Step B of Example 1, 0.08 g of 4-dimethylamino-pyridine and 2.55 g of dicyclohexylcarbodiimide was stirred for 5 hours at ambient temperature in methylene chloride and the urea formed was filtered off. The filtrate was concentrated to dryness under reduced pressure and the residue was taken up in ether, washed with a saturated aqueous solution of sodium bicarbonate, then with salted water, re-extracted with ether, dried and the solvents were eliminated under reduced pressure to obtain 4 g of crude product in the form of the base which was chromatographed over silica (eluent:ethyl acetate-triethylamine 98-2) to obtain 1.05 g of isomer A and 1.0 g of isomer B.

Isomer A: Preparation of the Hydrochloride 0.6 ml of an ethanol solution of hydrogen chloride (5.75N) were added to 0.90 g of isomer A in the form of the base in 8 ml of ethanol to obtain 0.7 g of the hydrochloride after crystallization in isopropanol. It melted at 174° C.

Analysis: $C_{23}H_{26}Cl_2N_2O$, HCl: 453.839.

| Calculated: | % C 53.62 | % H 5.35 | % N 8.93 | % S 6.82 | % Cl 15.07 |
|---|---|---|---|---|---|
| Found: | 53.4 | 5.6 | 8.6 | 6.7 | 14.8 |

Isomer B: Preparation of the Hydrochloride

The operation for isomer A was repeated with 0.90 g of isomer B in the form of the base to obtain 0.55 g of hydrochloride melting at 176° C.

EXAMPLE 23

[Trans(±)]3,4-dichloro-N-[2,3-dihydro-2-(1-piperidinyl)-1H-inden-1-yl]-N-methyl-benzene-acetamide and its hydrochloride STEP A:
[Trans(±)]2,3-dihydro-1-piperidinyl-1H-inden-2-ol At 50° C. and over 5 minutes, 50 ml of piperidine and 50 ml of water were added to 21.25 g of 2,3-epoxy-indane and the mixture was maintained for 2 hours with stirring at this temperature. The solution was then cooled to 20° C. and was saturated with sodium chloride. 5 ml of sodium hydroxide were added, followed by extraction with ether. The extracts were concentrated to dryness under reduced pressure and the residue was taken up in 200 ml of ethyl acetate at 40° C., filtered, dried, and the solvents were eliminated under reduced pressure. The residue was taken up in isopropyl ether, filtered and taken to dryness to obtain 26.82 g of crude product which was purified by chromatography over silica, (eluent: ethyl acetate with 1% of triethylamine) to obtain [trans(±)]2,3-dihydro-1-piperidinyl-1H-inden-2-ol melting at about 82° C.

STEP B:
[Trans(±)]2,3-dihydro-N-methyl-2-piperidinyl-1H-inden-1-amine

A solution of 4.34 g of the product of Step A and 3.7 ml of triethylamine in 30 ml of tetrahydrofuran was cooled to −20° C. and then over 7 minutes, 1.9 ml of methane sulfonyl chloride in 4 ml of tetrahydrofuran were added. Stirring was maintained for 15 minutes and then the temperature was allowed to return to 0° C. 17 ml of methylamine in 33% ethanol solution were added with stirring while allowing the temperature of the reaction mixture to return to ambient. After stirring for 25 hours, the solvent was eliminated under reduced pressure and the residue was taken up in 10 ml of salted water. 5 ml of sodium hydroxide were added and extraction was done with ethyl acetate. The extracts were concentrated to dryness to obtain 4.743 g of crude product which was dissolved in 23 ml of an ethanol solution of hydrogen chloride (1.68N). Crystallization was initiated and the crystals were separated, dried at 70° C. to obtain 9.12 g of [Trans(±)]2,3-dihydro-N-methyl-2-piperidinyl-1H-inden-1-amine melting at >260° C.

Analysis:

| Calculated: | % C 59.42 | % H 7.98 | % N 9.24 | % Cl 23.38 |
|---|---|---|---|---|
| Found: | 59.3 | 8.0 | 9.2 | 22.8 |

STEP C:
[Trans(±)]3,4-dichloro-N-[2,3-dihydro-2-(1-piperidinyl)-1H-inden-1-yl]-N-methyl-benzene-acetamide and its hydrochloride 0.533 g of 3,4-dichlorophenyl acetic acid and 0.422 g of carbonyldiimidazole were stirred for 1 hour in 5 ml of tetrahydrofuran and 0.6 ml of triethylamine and then 0.606 g of the product of Step B were added. The mixture was stirred for 16 hours and the solvent was eliminated under reduced pressure. The residue was taken up in 30 ml of ethyl acetate and was washed with a saturated aqueous solution of sodium bicarbonate, then with a saturated solution of sodium chloride. After drying and concentrating to dryness under reduced pressure, 0.981 g of crude product were obtained.

Preparation of Hydrochloride

The said base was dissolved in 5 ml of ethanol and 1.5 ml of a 1.68N solution of hydrogen chloride in ethanol were added. Crystallization was initiated and the crystals were separated, rinsed with ethanol then with ether, dried at 80° C. under reduced pressure to obtain 0.656 g of the hydrochloride melting at about 217° C.

Analysis:

| Calculated: | % C 60.87 | % H 6.00 | % N 6.17 | % Cl 23.43 |
|---|---|---|---|---|
| Found: | 60.7 | 6.0 | 6.0 | 23.3 |

EXAMPLE 24

[Trans(±)]3,4-dichloro-N-[2,3-dihydro-2-(4-methyl-1-piperazinyl-1H-inden-1-yl]-N-methyl-benzene-acetamide STEP A:
[Trans(±)]2,3-dihydro-1-(4-methyl-1-piperazinyl)-1H-inden-2-ol Using the procedure of Example 23, Step A, 14.57 g of 2,3-epoxy-indane and 12.4 ml of N-methyl piperazine were reacted to obtain 6.447 g of [trans(±)]2,3-dihydro-1-(4-methyl-1-piperazinyl)-1H-inden-2-ol melting at 132° C.

STEP B:
[Trans(±)]2,3-dihydro-N-methyl-2-(4-methyl-1-piperazinyl)-1H-inden-1-amine and its hydrochoride Using the procedure of Example 23, Step B, 4.64 g of the product of Step A were reacted to obtain 5.58 g of the expected product in the form of the base, then 6.79 g of hydrochloride melting at >260° C.

Analysis:

| Calculated: | % C 50.79 | % H 7.39 | % N 11.84 | % Cl 29.98 |
|---|---|---|---|---|
| Found: | 51.3 | 7.4 | 11.8 | 28.5 |

STEP C:
[Trans(±)]3,4-dichloro-N-[2,3-dihydro-2-(4-methyl-1-piperazinyl)-1H-inden-1-yl]-N-methyl-benzene-acetamide Using the procedure of Example 23 Step C, 0.720 g of the hydrochloride of Step B and 0.533 g of 3,4-dichlorophenyl acetic acid were reacted to obtain 1.070 g of [trans(±)]3,4-dichloro-N-[2,3-dihydro-2-(4-methyl-1-piperazinyl)-1H-inden-1-yl]-N-methyl-benzene-acetamide in the form of the base, then 0.866 g of its hydrochloride melting at 223° C.

Analysis: $C_{23}H_{27}Cl_2N_3O$, 2HCl: 505.318

| Calculated: | % C 54.67 | % H 5.78 | % N 8.31 | % Cl 28.06 |
|---|---|---|---|---|
| Found: | 54.5 | 5.9 | 8.2 | 27.5 |

EXAMPLE 25

[Trans(±)]3,4-dichloro-N-[2,3-dihydro-2-(dimethylamino)-1H-inden-1-yl]-N-methyl-benzene-acetamide and its hydrochloride

STEP A:
[Trans(±)]2,3-dihydro-1-(dimethylamino)-1H-inden-2-ol and its hydrochloride Using the procedure of Step A of Example 23, but after the extraction with ether and the elimination of the solvents under reduced pressure, the residue was taken up in ether and 70 ml of a 1.68N solution of hydrogen chloride in ethanol were added. Crystallization was initiated and after standing for 2 hours, the crystals were separated and rinsed with ethanol and then with ether to obtain 15.15 g of [trans(±)]2,3-dihydro-1-(dimethylamino)-1H-inden-2-ol and its hydrochloride which after crystallization from isopropanol melted at 184° C.

STEP B:
[Trans(±)]2,3-dihydro-N-methyl-2-(dimethylamino)-1H-inden-1-amine and its oxalate Using the procedure of Step B of Example 23, 4.27 g of the hydrochloride of Step A were reacted to obtain 3.87 g of the expected product in the form of the base.

Formation of the Oxalate 3.82 g of the base were dissolved in 2 ml of ethanol and 2.67 g of oxalic acid were added hot, and after rinsing with ethanol and then with ether, 3.22 g of the oxalate melting at 170° C. were obtained.

Analysis:

| Calculated: | % C 55.37 | % H 6.50 | % N 8.61 |
|---|---|---|---|
| Found: | 55.2 | 6.5 | 8.7 |

STEP C:
[Trans(±)]3,4-dichloro-N-[2,3-dihydro-2-(dimethylamino)-1H-inden-1-yl]-N-methyl-benzene-acetamide and its hydrochloride Using the procedure of Step C of Example 23, 0.650 g of the oxalate of Step B above and 0.533 g of 3,4-dichlorophenylacetic acid were reacted to obtain 0.834 g of the expected product in the form of the base, then 0.683 g of hydrochloride melting at about 233° C. (decomposes).

Analysis: $C_{20}H_{22}Cl_2N_2O$, HCl: 413.777.

| Calculated: | % C 58.06 | % H 5.60 | % N 6.77 | % Cl 25.70 |
|---|---|---|---|---|
| Found: | 58.2 | 5.6 | 6.7 | 25.9 |

EXAMPLE 26

[Trans(±)]3,4-dichloro-N-[2,3-dihydro-1,1-dimethyl-2-(1-pyrrolidinyl)-1H-inden-3-yl]-N-methyl-benzene-acetamide and its trans butene dioate

STEP A: Dimethyl-1,1-indene oxide

A mixture of 1,1-dimethyl indene [prepared as in Boschond et al, Canadian J. of Chem., Vol. 42, p. 1718 (1964)] in 40 ml of methylene chloride, 75 ml of a 10% aqueous solution of sodium bicarbonate and 5.45 g of sodium bicarbonate was cooled to 7° C. and 11.57 g of metachloroperbenzoic acid were added while maintaining the temperature at less than 10° C. Then the mixture was stirred for 22 hours at ambient temperature, filtered, decanted, and the aqueous phase was washed with methylene chloride. The combined organic phases were washed with a 10% aqueous solution of sodium thiosulfate, then with a 10% aqueous solution of sodium bicarbonate and then with water. After drying and eliminating the solvents under reduced pressure, 9.2 g of dimethyl-1,1-indene oxide were obtained which was utilized as is in the following step.

STEP B:
[Trans(±)]1,1-dimethyl-3-pyrrolidine-2-indanol

A mixture of 7 ml of pyrrolidine and 7 ml of water was added to 9 g of the product of Step A and the reaction medium was heated to 65° C. for 2 hours. After cooling, diluting with 10 ml of water and eliminating the excess of pyrrolidine under reduced pressure, extraction was done with ethyl acetate. The extracts were dried and concentrated to dryness under reduced pressure to obtain 10 g of crude product which was purified by chromatography over silica (eluent:n-hexane-ethyl acetate-triethylamine (27-70-3) to obtain [trans(±)]1,1-dimethyl-3-pyrrolidine-2-indanol melting at 86° C.

STEP C: Mesylate of [trans(±)]1,1-dimethyl-3-pyrrolidine-2-indanol 4.8 g of the product of Step B, 50 ml of tetrahydrofuran and 3.86 ml of triethylamine were cooled to −20° C. and 1.8 g of methane sulfonyl chloride in solution in 5 ml of tetrahydrofuran were added dropwise. The temperature was allowed to return to ambient and the reaction medium was stirred for 64 hours. It was then diluted with iced water and 2 ml of 0.1N sodium hydroxide were added. Extraction was done with ethyl acetate and the organic phase was washed with salted water, dried, and the solvents were eliminated under reduced pressure to obtain 6.9 g of mesylate of [trans(±)]1,1-dimethyl-3-pyrrolidine-2-indanol which was used as is for the following step.

STEP D:
[Trans(±)]2,3-dihydro-N-methyl-2-(1-pyrrolidinyl)-3,3-dimethyl-1H-inden-1-amine A mixture of 6.9 g of the product of Step C in 15 ml of a 35 to 40% aqueous solution of methylamine was heated for 18 hours at 70° C. in an autoclave (P=1.5 bar) and after cooling and diluting with water, extraction was done with ethyl acetate. The organic phase was washed with water, dried and concentrated under reduced pressure to obtain 6 g of crude [trans(±)]2,3-dihydro-N-methyl-2-(1-pyrrolidinyl)-3,3-dimethyl-1H-inden-1-amine which was purified by chromatography on silica (eluent:ethyl acetate-n-hexane-triethylamine, 60-37-3).

STEP E:

[Trans(±)]3,4-dichloro-N-[2,3-dihydro-1,1-dimethyl-2-(1-pyrrolidinyl)-1H-inden-3-yl]-N-methyl-benzene-acetamide and its trans butene dioate Using the procedure of Step D of Example 2, 0.570 g of the product of Step C and 0.668 g of 3,4-dichlorophenylacetic acid were reacted to obtain 1.232 g of the expected product in the form of its base. 1.064 g of this base were converted into the fumarate melting at 170° C.

Analysis: $C_{24}H_{28}Cl_2N_2O$, $C_4H_4O_4$: 547.483.

| | | | | |
|---|---|---|---|---|
| Calculated: | % C 61.43 | % H 5.89 | % N 5.12 | % Cl 12.95 |
| Found: | 61.3 | 6.0 | 5.1 | 12.9 |

EXAMPLE 27

[Trans(±)]N-[2,3-dihydro-1,1-dimethyl-2-(1-pyrrolidinyl)-1H-inden-3-yl]-N-methyl-4-nitrobenzene-acetamide and its trans butene dioate Using the procedure of Step D of Example 2, 0.489 g of [trans(±)]2,3-dihydro-N-methyl-2-(1-pyrrolidinyl)-3,3-dimethyl-1H-inden-1-amine of Step D of Example 26 and 0.471 g of p-nitrophenyl acetic acid were reacted to obtain 0.888 g of the expected product in the form of its base, then 0.433 g of fumarate melting at 161° C.

Analysis: $C_{24}H_{29}N_3O_3$. 1.25 $C_4H_4O_4$: 552.602.

| | | | |
|---|---|---|---|
| Calculated: | % C 63.03 | % H 6.20 | % N 7.60 |
| Found: | 62.8 | 6.3 | 7.5 |

EXAMPLE 28

[Trans(±)]N-[2,3-dihydro-1,1-dimethyl-3-(1-pyrrolidinyl)-1H-inden-2-yl]-N-methyl-4-nitrobenzene-acetamide and its hydrochloride

STEP A:

[Trans(±)]2,3-dihydro-1[methyl(benzyl)-amino]-3,3-dimethyl-1H-inden-2-ol 10.4 ml of N-benzylmethylamine in 50 ml of water were mixed with 12.4 g of 1,1-dimethyl indene oxide of Step A of Example 26 and the mixture was heated for 3 hours at 90° to 95° C. After cooling to 5° C., the aqueous phase was decanted off and the organic phase was taken up with ethyl acetate and extracted with a 1N aqueous solution of hydrochloric acid. The extract was neutralized with a saturated aqueous solution of sodium bicarbonate, then extracted with ethyl acetate, dried, and the solvents were eliminated under reduced pressure to obtain 10 g of crude [trans(±)]2,3-dihydro-1-[methyl(-benzyl)-amino]-3,3-dimethyl-1H-inden-2-ol which was purified by chromatography over silica (eluent:n-hexane-ethyl acetate 8-2) to obtain 8.86 g of the product.

STEP B: Mesylate of [trans(±)]1,1-dimethyl-3-benzylmethylamino-2-indanol 8.7 g of the product of Step A were cooled to −20° C. in 80 ml of methylene chloride and 13 ml of triethylamine, and 4.85 ml of methane sulfonyl chloride in 24 ml of methylene chloride were added dropwise. After stirring for 30 minutes at −20° C., the temperature was allowed to return to +3° C. and cold water was added. The organic phase was separated and washed with water, then dried and the solvents were eliminated under reduced pressure to obtain 13 g of mesylate of [trans(±)]1,1-dimethyl-3-benzylmethylamino-2-indanol which was used as is in the following step.

STEP C:

[Trans(±)]1,1-dimethyl-2-benzylmethylamino-3-pyrrolidine-indane

At ambient temperature, 30 ml of pyrrolidine in 30 ml of distilled water were added to 13 g of the product of Step B and the mixture was heated for 17 hours at 75° C., then cooled to ambient temperature. Excess pyrrolidine was evaporated off under reduced pressure and the reaction medium was saturated with sodium chloride, then extracted with ethyl acetate. The extracts were dried, and the solvents were eliminated under reduced pressure to obtain 13.5 g of crude product which was purified by chromatography over silica (eluent:n-hexane-ethyl acetate 8-2) to obtain 8.7 g of [trans(±)]1,1-dimethyl-2-benzylmethylamino-3-pyrrolidine-indane.

STEP D:

[Trans(±)]1,1-dimethyl-2-methylamino-3-pyrrolidino-indane 2.5 g of the product of Step C in 56.5 ml of methanol, and 4 ml of 37% hydrochloric acid were hydrogenated for 14 hours (p=185 mbar) in the presence of 1.7 g of activated charcoal with 10% palladium. After evaporating off the methanol under reduced pressure, taking up with water and neutralizing with triethylamine, extraction was done with ethyl acetate. The extracts were dried and the solvents were eliminated under reduced pressure to obtain 0.7 g of residue which was taken up in 5 ml of water. 6 ml of 32% sodium hydroxide were added, and extraction was done with ethyl acetate. The extracts were washed with an aqueous solution of sodium chloride, then dried and concentrated to dryness under reduced pressure to obtain 0.64 g of [trans(±)]1,1-dimethyl-2-methyl-amino-3-pyrrolidine-indane which was used as is for the following step.

STEP E:

[Trans(±)]N-[2,3-dihydro-1,1-dimethyl-3-(1-pyrrolidinyl-1H-inden-2-yl]-N-methyl-4-nitrobenzene-acetamide and its hydrochloride Using the procedure of Step C of Example 1, 0.386 g of the product of Step D and 0.371 g of p-nitrophenyl acetic acid were reacted to obtain after chromatography of the crude product over silica (eluent:ethyl acetate with 1% of triethylamine) 0.585 g of the expected product in the form of its base, then 0.483 g of its hydrochloride melting at 209° C.

Analysis: $C_{24}H_{29}N_3O_3$, HCl: 443.97.

| | | | | |
|---|---|---|---|---|
| Calculated: | % C 64.92 | % H 6.81 | % N 9.46 | % Cl 7.98 |
| Found: | 64.9 | 6.9 | 9.5 | 7.8 |

EXAMPLE 29

[Trans(±)]3,4-dichloro-N-[2,3-dihydro-1,1-dimethyl-3-(1-pyrrolidinyl)-1H-inden-2-yl]-N-methyl-benzene-acetamide and its trans butane dioate Using the procedure of Step D of Example 2, 0.570 g of the product of Step D of Example 28 and 0.668 g of 3,4-dichlorophenyl acetic acid were reacted to obtain 1.232 g of the expected product in the form of its base, then 0.502 g of its fumarate melting at 170° C.

Analysis: $C_{24}H_{28}Cl_2N_2O$, $C_4H_4O_4$: 547.483.

| | | | | |
|---|---|---|---|---|
| Calculated: | % C 61.43 | % H 5.89 | % N 5.12 | % Cl 12.93 |
| Found: | 61.3 | 6.0 | 5.0 | 12.9 |

EXAMPLE 30

[Trans(±)]N-[4-bromo-2,3-dihydro-2-(1-pyrrolidinyl)-1H-inden-1-yl]-3,4-dichloro-N-methyl-benzene-acetamide and its hydrochloride

STEP A: 3-bromo-1aH-indeno[1,2-b]oxirene

Using the procedure of Step A of Example 26, 13.2 g of 7-bromo-1H-indene were reacted to obtain 17.32 g of 3-bromo-1aH-indeno[1,2-b]oxirene which was used as is for the following step.

STEP B:
[Trans(±)]4-bromo-2,3-dihydro-1-(1-pyrrolidinyl)-1H-inden-2-ol and its hydrochloride Using the procedure of Step B of Example 26, the product of Step A was reacted to obtain 7.88 g of crude product which was converted into its hydrochloride with 16 ml of a 1.68N ethanol solution of hydrogen chloride. The product melted at 229° C. (decomposes).

STEP C:
[Trans(±)]4-bromo-2,3-dihydro-N-methyl-2-(1-pyrrolidinyl)-1H-inden-1-amine and its hydrochloride Using the procedure of Steps C and D of Example 26, the product of Step B was reacted to obtain 4.12 g of crude product in the form of the base which was converted into the hydrochloride with 4 ml of an ethanol solution of hydrogen chloride (about 6.6N) to obtain 3.82 g of the hydrochloride melting at about 240° C.

STEP D:
[Trans(±)]N-[4-bromo-2,3-dihydro-2-(1-pyrrolidinyl)-1H-inden-1-yl]-3,4-dichloro-N-methyl-benzene-acetamide and its hydrochloride Using the procedure of Step C of Example 1, 0.533 g of 3,4-dichlorophenyl acetic acid, 0.421 g of carbonyldiimidazole and 0.735 g of the hydrochloride of Step C were reacted to obtain 0.876 g of product in the form of the base, then 0.587 g of its hydrochloride melting at 208° C.

Analysis: $C_{22}H_{23}BrCl_2N_2O$, HCl: 547.483.

| | | | | | |
|---|---|---|---|---|---|
| Calculated: | % C 50.94 | % H 4.66 | % N 5.40 | % Cl 20.50 | % Br 15.40 |
| Found: | 51.1 | 4.6 | 5.3 | 20.3 | 15.4 |

EXAMPLE 31

[Trans(±)]N-[5-chloro-2,3-dihydro-2-(1-pyrrolidinyl)-1H-inden-1-yl]-3,4-dichloro-N-methyl-benzene-acetamide and its hydrochloride

STEP A:
[Trans(±)]4-chloro-1aH-indeno[1,2-b]oxirene

Using the procedure of Step A of Example 26, 10.05 g of 6-chloro-1H-indene were reacted to obtain 14.2 g of [trans(±)]4-chloro-1aH-indeno[1,2-b]oxirene which was used as is for the following step.

STEP B:
[Trans(±)]5-chloro-2,3-dihydro-1-(1-pyrrolidinyl)-1H-inden-2-ol and its hydrochloride Using the procedure of Step B of Example 26, the product of Step A was reacted to obtain 4.48 g of the expected product in the form of a base which was converted into its hydrochloride with 11 ml of a 0.68N ethanol solution of hydrogen chloride to obtain 3.52 g of the expected hydrochloride melting at 159° C.

STEP C:
[Trans(±)]5-chloro-2,3-dihydro-N-methyl-2-(1-pyrrolidinyl)-1H-inden-1-amine and its oxalate Using the procedure of Steps C and D of Example 26, the product of Step B was reacted to obtain 3.83 g of the expected product in the form of a base, then 4.38 g of oxalate by the addition of 2.3 g of dihydrated oxalic acid melting about 165° C.

STEP D:
[Trans(±)]N-[5-chloro-2,3-dihydro-2-(1-pyrrolidinyl)-1H-inden-1-yl]-3,4-dichloro-N-methyl-benzene-acetamide and its hydrochloride Using the procedure of Step C of Example 1, 0.533 g of 3,4-dichlorophenyl acetic acid, 0.421 g of carbonyldiimidazole and 0.772 g of the oxalate of Step C were reacted to obtain 0.940 g of the expected product in the form of a base, then 0.760 g of hydrochloride melting at 228° C.

Analysis: $C_{22}H_{23}Cl_3N_2O$, HCl: 474.26.

| | | | | |
|---|---|---|---|---|
| Calculated: | % C 55.72 | % H 5.10 | % N 5.91 | % Cl 22.90 |
| Found: | 56.0 | 5.2 | 5.9 | 29.6 |

EXAMPLE 32

Tablets were prepared containing 200 mg of the product of Example 1 and sufficient excipient of lactose, talc, starch and magnesium stearate for a final weight of 800 mg.

EXAMPLE 33

An injectable solution (intra-muscular route) was prepared containing 50 mg of the product of Example 25 and sufficient sterile solvent for a volume of 5 ml.

PHARMACOLOGICAL STUDY

1) Liaison with the opiated receptor K in vitro

Membrane residue prepared from the cerebella of guinea-pigs preserved at −30° C. (possibly up to about 30 days) were used and these residues were suspended in Tris pH 7.7 buffer. Fractions of 2 ml were distributed in haemolysis tubes and $9^3H$ ethylketocyclazocine 1 nM was added together with the product to be studied. The product was first tested at $5 \times 10^{-6}$M (in triplicate). When the product tested displaced by more than 50% the radioactivity bonded specifically to the receptor, it was again tested in a range of 7 doses to determine the dose which inhibited by 50% the radioactivity bonded specifically to the receptor. In this way, the 50% inhibiting concentration was determined. The non-specific liaison was determined by addition of the product known by the name U-50488 H (Lahti et al. 1982, Life Sci. 31, 2257) at $10^{-5}$M (in triplicate). It was then incubated at 25° C. for 40 minutes, replaced on the waterbath at 0° C. for 5 minutes, filtered under vacuum, rinsed with the Tris pH 7.7 buffer, and the radioactivity was counted in the presence of scintillating Trition.

The result was expressed in the following Table directly as 50% inhibiting concentration ($IC_{50}$), (i.e., as the concentration of the product studied, expressed in nM, necessary to displace 50% of the specific radioactivity fixed on the receptor studied.

| Product of example | $IC_{50}$ in nM |
|---|---|
| 1 | 1.8 |
| 5 | 3 |
| 6 | 7.5 |
| 8 | 7.1 |
| 9 | 2.7 |
| 14 | 3.8 |
| 16 | 5 |
| 22 | 7.1 |
| 25 | 2.2 |
| 29 | 5.6 |

2) Analgesic activity

Female mice weighing 22 to 24 g were placed one by one on a copper plate maintained at 56° C. and the reaction to the pain was seen by the animal licking its front paws. The time of this reaction was noted and only the mice reacting in less than 8 seconds were retained. The animals were distributed in homogeneous groups and treated with the product under study administered orally, one group receiving only the vehicle. The time of reaction to the pain was again measured 30 to 60 minutes after the treatment. The active dose or $AD_{100}$ was the dose which increased the reaction time by 100% 30 minutes after the treatment, taking account of the variation of the reaction times of the control animals. For the product of Example 1, the $AD_{100}$ was 50 mg/kg.

3) Study of the hypotensive activity on the anaesthetized rat

Male Sprague Dawley (CR) rats were anaestherized intra-peritoneally with 60 mg/kg of sodium pentobarbital and a jugular vein was catheterized for injection of the product, and a carotid artery was catheterized to register the arterial pressure. The product under test was dissolved in 10% of ethanol and then was injected at a volume of 1 ml/kg. The pressure was noted at times of 5 minutes and 30 minutes after the injection of the product. The following Table indicates the variations expressed as a percentage of the arterial pressure after administration of the product under test to the arterial pressure of the initial control.

Results:

| Product of example | dose mg/kg | 5 min. after administration | 30 min. after administration |
|---|---|---|---|
| 1 | 10 | −13 | −19 |
|  | 1 | −19 | −23 |
| 4 | 10 | −26 | −14 |
| 5 | 10 | −25 | −10 |
|  | 1 | −20 | −20 |
| 8 | 1 | −25 | −27 |
| 14 | 1 | −22 | −26 |
| 9 | 10 | −32 | −31 |

4) Measurement of the diuretic activity

Male rats of Sprague Dawley strain weighing 180 to 200 g were not fed for 17 hours before the test, but received water ad libitum. Groups of 8 animals were set up for each dose tested and the rats received the product under test or its vehicle orally. The urinary volume was measured every hour for the 5 hours following the administration of the product. At the end of this period, the urines were collected and the activity of the product was expressed as a percentage of variation calculated on the urinary volume corresponding to the period $t_{1h}-t_{5h}$. The following results were obtained:

| Product of example | dose mg/kg | percentage of variation of the urinary volume |
|---|---|---|
| 1 | 5 | −188 |
| 1 | 5 | −190 |
| 8 | 5 | −130 |
|  | 2.5 | −124 |
| 14 | 5 | −68 |
| 9 | 10 | −74 |

5) Anti-arrythmic activity in the rat

Male rats weighing 300 to 350 g anaesthetized intra-peritoneally with 1.20 g/kg of urethane were tracheotomized and submitted to artificial respiration (40 to 50 insufflations of 3 ml/minute). Needles were implanted sub-cutaneously to register the electro-cardiogram of the rats on the DII derivation signal. The product under test was administered intravenously and 5 minutes after the administration of the product, the jugular vein of the rats was perfused with 10 μg/kg from 0.2 ml of an aconitine solution and the time of appearance of disturbances of the cardiac rhythm was noted. The results expressed as a percentage of the extension of the time of appearance of the disturbances of the cardiac rhythm in relation to the controls and as a function of the dose of the product tested are in the following Table which show that the tested products of the application are endowed with good anti-arrythmic properties.

| Product of example | Dose mg/kg | Percentage of extension of time |
|---|---|---|
| 1 | 10 | +31.4 |
|  | 5 | +20.6 |
| 5 | 10 | +15.6 |
| 8 | 5 | +23 |
| 9 | 10 | +34.6 |
|  | 5 | +32 |

Various modifications of the products and method of the invention may be made without departing from the spirit or scope thereof and it is to be understood that the invention is intended to be limited only as defined in the appended claims.

What we claim is:

1. A compound selected from the group consisting of enantiomers and diastereoisomer forms and mixtures thereof of the formula

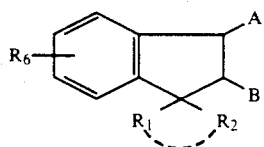

wherein $R_1$ and $R_2$ together with the carbon atom to which they are attached form tetrahydropyran $R_6$ is selected from the group consisting of hydrogen, halogen and alkyl and alkoxy of 1 to 5 carbon atoms, one of A and B has the formula

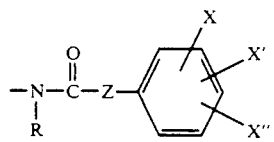

and the other is pyrrolidinyl, R is hydrogen or alkyl of 1 to 5 carbon atoms, Z is selected from the group consisting of $-(CH_2)_n-$, $-CH_2O-$ and branched alkylene of 2 to 8 carbon atoms, n is an integer from 0 to 5, X, X' and X" are individually selected from the group consisting of hydrogen, alkyl and alkoxy of 1 to 5 carbon atoms, halogen, $-OH$, $-CF_3$, $-NO_2$, $-NH_2$, mono- and dialkylamino of 1 to 4 alkyl carbon atoms and sulfamino and their non-toxic, pharmaceutically acceptable acid addition salts.

2. A compound of claim 1 wherein A and B have a trans configuration.

3. A compound of claim 1 wherein R is hydrogen, methyl or ethyl and Z is $-(CH_2)_n-$,

or $-CH_2O-$ and n is 0 or 1.

4. A compound of claim 1 wherein X, X' and X" are individually selected from the group consisting of hydrogen, methyl, ethyl, methoxy, ethoxy, $-NO_2$, $-CF_3$, Cl and sulfamino.

5. A compound of claim 1 selected from the group consisting of [trans($\pm$)]3,4-dichloro-N-[2,2',3,3',5',6'-hexahydro-2-(1-pyrrolidinyl)-spiro[1H-inden-1,4'-(4H)-pyran]-3-yl]-N-methyl-benzene-acetamide and its hydrochloride and (E) butenedioate of [trans($\pm$)]3,4-dichloro-N-[2,2',3,3',5',6'-hexahydro-3-(1-pyrrolidinyl)-spiro[1H-inden-1,4'-(4H)-pyran]-2-yl]-N-methyl-benzene-acetamide.

6. A central analgesic composition comprising a central analgesically effective amount of a compound of claim 1 and an inert pharmaceutical carrier.

7. A composition of claim 6 wherein in the compound of formula 1, A and B have a trans configuration.

8. A composition of claim 6 wherein in the compound of formula 1, R is hydrogen, methyl or ethyl and Z is $-(CH_2)_n-$,

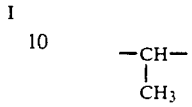

or $-CH_2O-$ and n is 0 or 1.

9. A composition of claim 6 wherein in the compound of formula 1, X, X' and X" are individually selected from the group consisting of hydrogen, methyl, ethyl, methoxy, ethoxy, $-NO_2$, $-CF_3$, $-Cl$ and sulfamino.

10. A composition of claim 6 wherein the active compound is selected from the group consisting of [trans($\pm$)]3,4-dichloro-N-[2,2',3,3',5',6-hexahydro-2-(1-pyrrolidinyl)-spiro[1H-inden-1,4'-(4H)-pyran]-3-yl]-N-methyl-benzene-acetamide and its hydrochloride and (E) butenedioate of [trans($\pm$)]3,4-dichlor-N-[2,2',3,3',5',6'-hexahydro-3-(1-pyrrolidinyl)-spiro[1H-inden-1,4'-(4H)-pyran]-2-yl]-N-methyl-benzene-acetamide.

11. A method of inducing central analgesic activity in warm-blooded animals comprising administering to warm-blooded animals an analgesically effective amount of a compound of claim 1.

12. A method of claim 11 wherein A and B have a trans configuration.

13. A method of claim 11 wherein R is hydrogen, methyl or ethyl and Z is $-(CH_2)_n-$,

or $-CH_2O-$ and n is 0 or 1.

14. A method of claim 11 wherein X, X' and X" are individually selected from the group consisting of hydrogen, methyl, ethyl, methoxy, ethoxy, $-NO_2$, $-CF_3$, Cl and sulfamino.

15. A method of claim 11 wherein the active compound is selected from the group consisting of [trans($\pm$)]3,4-dichloro-N-[2,2',3,3',5',6'-hexahydro-2-(1-pyrrolidinyl)-spiro[1H-inden-1,4'-(4H)-pyran]-3-yl]-N-methyl-benzene-acetamide and its hydrochloride and (E) butenedioate of [trans($\pm$)]3,4-dichloro-N-[2,2',3,3',5',6'-hexahydro-3-(1-pyrrolidinyl)-spiro[1H-inden-1,4'-(4H)-pyran]-3-yl]-N-methyl-benzene-acetamide.

16. A method of inducing diuresis activity in warm-blooded animals comprising administering to warm-blooded animals a diuretically effective amount of a compound of claim 1.

17. A method of treating arrythmia in warm-blooded animals comprising administering to warm-blooded animals an anti-arrythmically effective amount of a compound of claim 1.

* * * * *